United States Patent [19]

Albrecht et al.

[11] Patent Number: 4,584,132
[45] Date of Patent: Apr. 22, 1986

[54] 1-(N-PHOSPHINYLCARBAMOYL) β-LACTAM ANTIBACTERIAL AGENTS

[75] Inventors: Harry A. Albrecht, Towaco; Frederick M. Konzelmann, West Paterson; Dennis D. Keith, Montclair, all of N.J.

[73] Assignee: Hoffmann-La Roche Inc., Nutley, N.J.

[21] Appl. No.: 521,519

[22] Filed: Aug. 9, 1983

[51] Int. Cl.$^4$ .................. C07F 9/65; A61K 31/675
[52] U.S. Cl. .................. 260/239 A; 260/245.4; 260/330.3; 260/330.9; 544/243; 544/337; 514/86; 514/85
[58] Field of Search ............ 260/239 A, 245.4, 330.3, 260/330.9; 544/337, 243

[56] References Cited

U.S. PATENT DOCUMENTS 4,478,749 10/1984 Koster et al. .................. 260/239 A

FOREIGN PATENT DOCUMENTS 0062876 10/1982 European Pat. Off. .

Primary Examiner—Mark L. Berch
Attorney, Agent, or Firm—Jon S. Saxe; George M. Gould; Bernard S. Leon

[57] ABSTRACT

A novel family of β-lactam antibacterials, synthetic methods and intermediates useful in the production of such antibacterials, and the use of such compounds as antibacterials are disclosed. The novel compounds have the formula

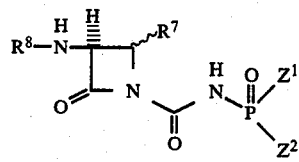

wherein,
$Z^1$ is a group —$OR^1$, —$NR^3R^4$, or —$SR^5$;
$Z^2$ is a group —$OR^2$, —$NR^3R^4$, or —$SR^6$;
$R^1$ and $R^2$ may be either the same or different and each is H, lower alkyl, aralkyl, aryl or heteroaryl;
$R^3$ and $R^4$ may be either the same or different and each is H, lower alkyl, aralkyl, aryl or heteroaryl;
$R^5$ and $R^6$ may be either the same of different and each is H, lower alkyl, aralkyl, aryl or heteroaryl;
$R^7$ is H, lower alkyl, or lower alkoxycarbonyl; and,
$R^8$ is acyl;

as well as pharmaceutically acceptable salts thereof.

27 Claims, No Drawings

1-(N-PHOSPHINYLCARBAMOYL) β-LACTAM ANTIBACTERIAL AGENTS

This invention relates to a novel family of β-lactam antibacterials, synthetic methods and intermediates useful in the production of such antibacterials, and the use of such compounds as antibacterial agents. The invention relates more particularly to substituted monocyclic, N-phosphinylcarbamoyl β-lactam derivatives.

The novel family of β-lactam antibacterials of the present invention encompasses compounds of the formula

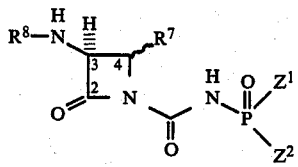

wherein:
$Z^1$ is a group $-OR^1$, $-NR^3R^4$, or $-SR^5$;
$Z^2$ is a group $-OR^2$, $-NR^3R^4$, or $-SR^6$;
$R^1$ and $R^2$ may be either the same or different and each is H, lower alkyl, aralkyl, aryl or heteroaryl;
$R^3$ and $R^4$ may be either the same or different and each is H, lower alkyl, aralkyl, aryl or heteroaryl;
$R^5$ and $R^6$ may be either the same or different and each is H, lower alkyl, aralkyl, aryl or heteroaryl;
$R^7$ is H, lower alkyl, or lower alkoxycarbonyl; and,
$R^8$ is acyl The invention is also considered to encompass pharmaceutically acceptable salts of compounds of formula I. Examples of salts provided by the present invention are salts with bases; for example, alkali metal salts such as the sodium salt and the potassium salt, the ammonium salt, alkaline earth metal salts such as the calcium salt, salts with organic bases such as salts with amine (e.g. salts with N-ethylpiperidine, procaine, dibenzylamine, N,N'-dibenzylethylethylenediamine, alkylamines or dialkylamines) and salts with amino acids (e.g. salts with arginine or lysine).

As used in this specification, the term "lower alkyl" refers to both straight and branched chain hydrocarbon groups having 1 to 8 and preferably 1 to 4 carbon atoms, which may be substituted or unsubstituted, such as, for example, methyl, ethyl, propyl, isopropyl, tentiary butyl and the like.

As used herein, the term "lower alkoxy" refers to alkoxy groups wherein the alkyl substituent is a lower alkyl group as defined hereinbefore. Exemplary lower alkyl groups are methoxy, ethoxy, propoxy and the like.

As used herein, the term "lower alkoxycarbonyl" refers to alkoxycarbonyl groups wherein the alkyl substituent is a lower alkyl as defined hereinbefore. Exemplary lower alkoxycarbonyl groups are methoxy carbonyl, ethoxycarbonyl and the like.

As used herein, the term "aralkyl" refers to groups comprising a lower-alkyl residue substituted by one or more aryl or substituted aryl groups, such as, for example, phenyl methyl, phenylethyl, phenylpropyl, phenylisopropyl, phenyl-tertiary butyl, hydroxy phenyl methyl and the like.

As used herein, the term aryl refers to a carbocyclic aromatic group, which can be substituted or unsubstituted, such as, for example, phenyl, hydroxy phenyl, tolyl, chlorophenyl and the like.

As used herein, the term "heteroaryl" refers to a substituted or unsubstituted 5, 6 or 7 membered heterocyclic ring containing 1, 2, 3 or 4 nitrogen, oxygen or sulfur atoms, such as, for example, thienyl, furyl, pyrrolyl, pyrazinyl, thiazolyl, pyrimidinyl, tetrazolyl and the like.

The term "acyl", as used herein, means and includes all organic radicals derived from an organic acid (i.e., a carboxylic acid) by removal of the hydroxyl group. Although the group $R^8$ may be any of many acyl radicals, certain acyl groups are preferred.

Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), Belgian Pat. No. 866,038 published Oct. 17, 1978, Belgian Pat. No. 867,994, published Dec. 11, 1978, U.S. Pat. No. 4,152,432, issued May 1, 1979, U.S. Pat. No. 3,971,778, issued July 27, 1976, and U.S. Pat. No. 4,172,199, issued Oct. 23, 1979. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R^9$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

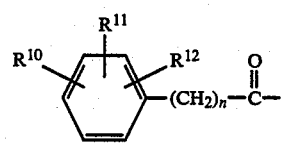

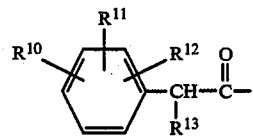

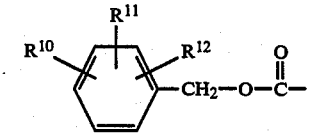

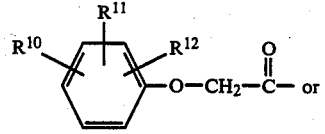

-continued

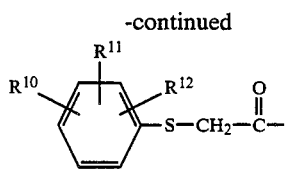

wherein n is 0, 1, 2 or 3; $R^{10}$, $R^{11}$, and $R^{12}$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R^{13}$ is amino, hydroxyl, a carboxyl salt, protected carboxyl, formyloxy, a sulfo salt, a sulfoamino salt, azido, or halogen.

Preferred carbocyclic aromatic acyl groups include those having the formula

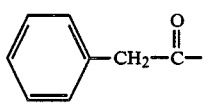

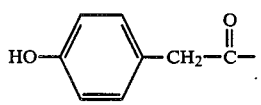

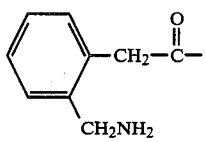

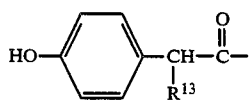

($R^{13}$ is preferably an amino group, a hydroxy group, or a carboxyl salt or sulfo salt) and

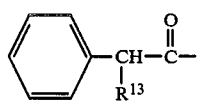

($R^{13}$ is preferably an amino group, a hydroxy group, or a carboxyl salt or sulfo salt).

(c) Heteroaromatic groups having the formula

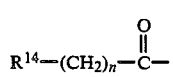

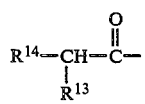

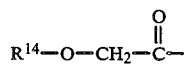

-continued

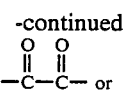 or wherein n is 0, 1, 2 or 3; $R^{13}$ is as defined above; and $R^{14}$ is a substituted or unsubstituted 5-, 6- or 7-membered heterocyclic ring containing 1, 2, 3 or 4 (preferably 1 or 2) nitrogen, oxygen and sulfur atoms. Exemplary heterocyclic rings are thienyl, furyl, pyrrolyl, pyridinyl, pyrazinyl, thiazolyl, morpholinyl, pyrimidinyl and tetrazolyl. Exemplary substituents are halogen, hydroxyl, nitro, amino, cyano, trifluoromethyl, alkyl of 1 to 4 carbon atoms, or alkoxy of 1 to 4 carbon atoms.

Preferred heteroaromatic acyl groups include those groups of the above formulas wherein $R^{14}$ is 2-amino-4-thiazolyl, 2-amino-5-halo-4-thiazolyl, 4-aminopyrimidin-2-yl, 2-amino-1,3,4-thiadiazol-5-yl, 2-thienyl or 2-furanyl.

(d) [[(4-Substituted-2,3-dioxo-1-piperazinyl)-carbonyl]amino]arylacetyl groups having the formula

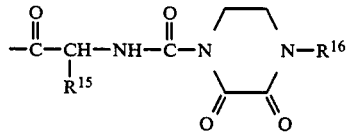

wherein $R^{15}$ is an aromatic group (including carbocyclic aromatics such as those of the formula

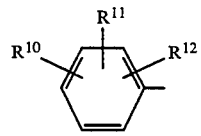

and heteroaromatics as included within the definition of $R^{14}$); and $R^{16}$ is alkyl, substituted alkyl (wherein the alkyl group is substituted with one or more halogen, cyano, nitro, amino or mercapto groups).

(e) (Substituted oxyimino)arylacetyl groups having the formula

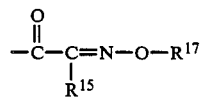

wherein $R^{15}$ is as defined above and $R^{17}$ is hydrogen, alkyl, cycloalkyl, alkylaminocarbonyl, arylaminocarbonyl (i.e.,

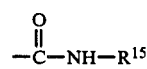

wherein $R^{15}$ is as defined above) or substituted alkyl (wherein the alkyl group is substituted with 1 or more halogen, cyano, nitro, amino, mercapto, alkylthio, aromatic group (as defined by $R^{15}$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, or dialkoxyphosphinyl substituents).

(f) (Acylamino)arylacetyl groups having the formula

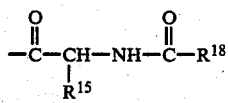

wherein R¹⁵ is as defined above and R¹⁸ is

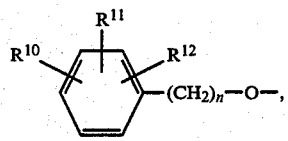

amino, alkylamino, (cyanoalkyl)amino, or acylamino.

Preferred (acylamino)arylacetyl groups of the above formula include those groups wherein R¹⁸ is amino, or acylamino. Also preferred are those groups wherein R¹⁵ is phenyl or 2-thienyl.

(g) [[[3-Substituted-2-oxo-1-imidazolidinyl]carbonyl]amino]arylacetyl groups having the formula

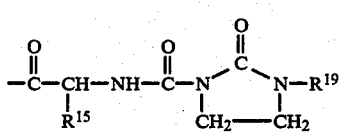

wherein R¹⁵ is as defined above and R¹⁹ is hydrogen, alkylsulfonyl, arylmethyleneamino (i.e., —N=CH—R¹⁵ wherein R¹⁵ is as defined above),

(wherein R²⁰ is hydrogen, alkyl or halogen substituted alkyl), aromatic group (as defined by R¹⁵ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein R¹⁵ is phenyl or 2-thienyl. Also preferred are those groups wherein R¹⁹ is hydrogen, methylsulfonyl, phenylmethyleneamino or 2-furylmethyleneamino.

It will be observed that compounds of formula I have a chiral center at the position 3 carbon atom of the β-lactam ring. In compounds encompassed by the invention, the stereo configuration of the position 3 chiral carbon atom is the same as that of the position 6 carbon atom in naturally occurring penicillins, such as penicillin G, and of the position 7 carbon atom in naturally occurring cephalosporins, such as cephalosporin C. Pursuant to convention, this stereo configuration of the position 3 carbon atom in compounds of formula I is designated the "S" configuration.

Mixtures of the S and R isomers of Compound I, such as racemic mixtures, are also considered to be within the scope of the invention.

The group R⁷, which is a substituent of the position 4 carbon atom, may be either cis or trans with respect to the acylamino group attached to the position 3 carbon atom.

β-lactam compounds according to the invention have activity against a broad spectrum of both gram-negative and gram-positive bacteria.

The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular and as a suppository.

Compounds of Formula I can be prepared in accordance with the following general synthetic scheme, which uses as starting material known compounds having the formula

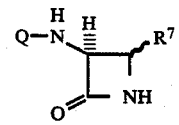

wherein Q is any known amino protecting group, such as, for example, benzyloxycarbonyl (CBZ) or tert-Butyloxycarbonyl (t-BOC), and wherein R⁷ is the same as hereinbefore described. Convenient syntheses of compounds of formula II are given by Floyd et al., J. Org. Chem., 47, (1982) 5160–7 and in European Pat. No. 62,876, at pages 23–24.

Initially, the amino protecting group is removed in a known per se manner, for example, in the case of CBZ by hydrogenation in the presence of a palladium over carbon catalyst and in the case of t-BOC by hydrolysis in the presence of an acid such as trifluoroacetic acid, to yield an intermediate of the formula

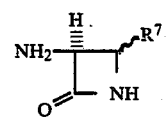

which is preferably not isolated, but reacted in situ.

The desired substitutent R⁸ is next introduced by reacting a compound of formula III with a carboxylic acid from which R⁸ is derivable, or an active derivative thereof, such as a corresponding acid halide, anhydride or active ester, employing known per se methods, to yield a compound of formula

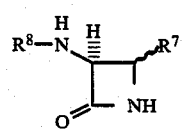

The intermediate IV is next condensed with dichlorophosphinylisocyanate, a known compound, to yield a compound of formula

V

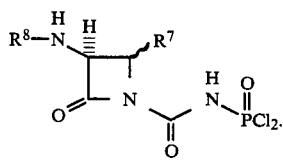

This condensation is conveniently carried out in solvents such as acetonitrile, tetrahydrofuran, methylenechloride, p-dioxane, dimethylformamide, chloroform and the like, at temperatures in the range between about −70° C. to 80° C., preferably in the range between about −10° C. and 30° C.

Where, in the desired compound of formula I, $Z^1$ is the same as $Z^2$, a compound of formula V is next reacted with an appropriate nucleophile such as water, an alcohol, a thiol or ammonia or a primary or secondary amine, to yield the product. This nucleophile is conveniently added in excess, except where such nucleophile is reactive toward the β-lactam function, for example, dimethyl amine, in which case two molar equivalents should be used. This reaction is conveniently carried out in the presence of a base, for example, triethylamine or pyridine, at temperatures in the range between about −78° C. and 30° C., depending upon the reagent with which the compound of formula V is reacted. The solvent employed for this reaction can be any of those useful in the above described condensation of the intermediate IV and, preferably, this further reaction is carried out in situ using the same solvent as used for the condensation of the intermediate. Appropriate alcohols are, for example methanol or ethanol. Appropriate thiols might be, for example, methane thiol or ethane thiol.

Appropriate amines might be, for example, methyl amine of dimethyl amine.

Where $Z^1$ is not the same as $Z^2$, a compound of formula V can first be reacted with approximately an equimolar quantity of an appropriate alcohol, mono or disubstituted amine, or thiol, in order to introduce a first Z group. The other Z group is next introduced by further reacting the intermediate produced above with water, or an appropriate alcohol, thiol, or mono or disubstituted amine. The reactions conditions employed here can be the same as those described above for syntheses where $Z^1$ is the same as $Z^2$. Similarly, the alcohols, thiols and amines can be the same as described above. If necessary, the product can be purified by chromatographic methods.

As a further alternative, where $Z^1$ is not the same as $Z^2$ and where $Z^1$ is alkoxy, an intermediate of formula IV can be condensed with an isocyanate of the formula

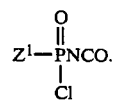

(Snytheses for isocyanates of this kind are disclosed in Narbut, A; Derkach, G. I., Zh. Obshch. Khim., 38 (1968) 1321-4.) The resulting condensation product is then further reacted with water, an alcohol, thiol or amine to yield the final product, as exemplified in the following scheme I. Here again the reaction conditions, solvents, alcohols, thiols and amines can be the same as those previously set forth with regard to syntheses where $Z^1$ is the same as $Z^2$.

Scheme I

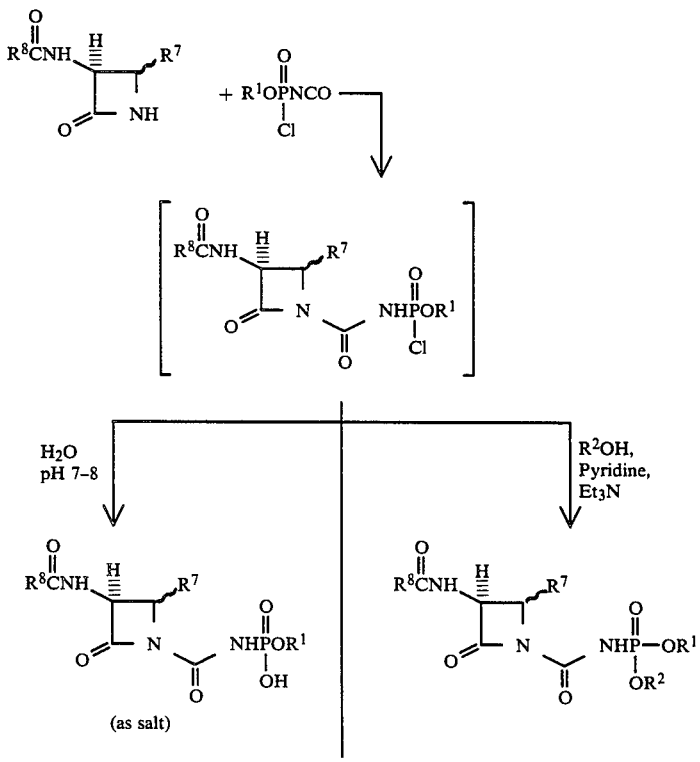

Scheme I

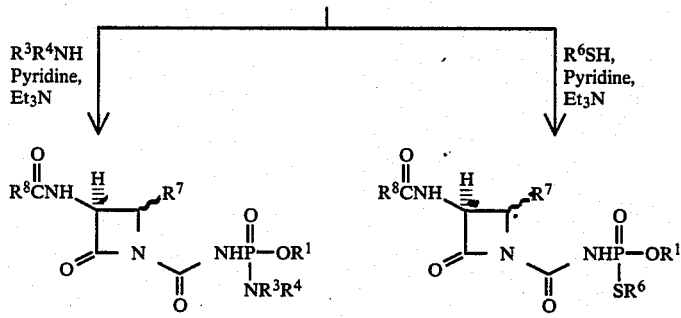

In another alternative synthetic scheme, the groups $Z^1$ and $Z^2$ are introduced into the isocyanate reactants prior to condensation with the intermediate of formula IV.

Thus, compounds of formula I can be made by reacting a compound of formula IV with a compound of formula

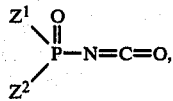           VII

This reaction is conveniently carried out in aprotic solvents such as methylene chloride, tetrahydrofuran, p-dioxane, acetonitrile, dimethoxyethane, dimethylformamide and the like, at temperatures in the range between about −20° C. and 80° C. Isocyanates of formula VII are generally known and are disclosed, for example, by Kirsanov et al., Zhur. Obshch. Khim. 27, (1957), p. 1002.

It should be recognized that the syntheses described above can, generally, be modified so that the phosphoramidic group is introduced prior to the introduction of the acylamino group. This is done by starting with an intermediate of formula II rather than one of Formula IV. The reaction conditions and solvents employed in this modification of the reaction scheme will, of course, be similar to those previously described for the introduction of the phosphoramidic group. After the introduction of this group, the amino protecting group Q can be removed in a known per se manner and the resulting intermediate reacted with an appropriate acid chloride or the like, in a manner analogous to that hereinbefore described, in order to introduce the acylamino group $R^8$.

Thus, for example, where $Z^1$ and $Z^2$ are both methoxy groups, a compound of formula II can be reacted first with dichlorophosphinylisocyanate and then methanol in the presence of triethylamine and pyridine to yield a compound of the formula

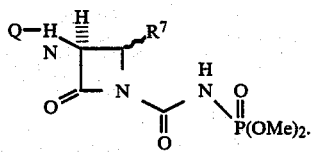           VIII

This intermediate is then deprotected and acylated to yield the product of formula I.

The following examples are specific embodiments of the invention.

EXAMPLE 1

Synthesis of (S)-N-[1-[[(Dimethoxyphosphinyl)amino]carbonyl]-2-oxo-3-azetidinyl benzeneacetamide (a) A mixture of 5.50 g (0.025 mol) of (S)-(2-oxo-3-azetidinyl) carbamic acid phenylmethyl ester, 250 mL of ethanol, and 2.0 g of 10% palladium on carbon catalyst was hydrogenated (2 hours) on a Parr apparatus at an initial gauge pressure of 50 psi. After filtration of the catalyst, the solution was concentrated to dryness under reduced pressure. A mixture of the residue with 4.2 mL (0.03 mol) of triethylamine and 30 mL of DMF was stirred and cooled in ice. A solution of 3.88 g (0.025 mol) of phenylacetyl chloride in 25 mL of ethanol-free chloroform was added over a period of 30 minutes. The mixture was stirred another 30 minutes with cooling, and then for 2.5 hours at room temperature. The chloroform was evaporated under reduced pressure, and 300 mL of ether was added to the residue. The mixture was cooled in ice for 20 minutes. The precipitate was filtered and washed successively with ether, aqueous $NaHCO_3$ solution, water, and ether. After drying in the air, the solid (2.15 g) was recrystallized from 50 mL of ethanol to obtain 1.86 g of pure (S)-N-(2-oxo-3-azetidinyl)benzeneacetamide, m.p. 194°–195° C.

(b) A mixture of 204 mg (1 mmol) of (S)-N-(2-oxo-3-azetidinyl)benzene acetamide, 4 mL of dry acetonitrile, 0.64 mL (4.8 mmol) of triethylamine and 0.16 mL (1.2 mmol, based on 85% purity) of phosphorisocyanatidic acid dimethyl ester was stirred at 45° C. for 5 minutes to obtain complete solution and kept at room temperature for 2 hours. An additional 0.08 mL (0.6 mmol) portion of phosphorisocyanatidic acid dimethyl ester was then added and the reaction stirred for another 2 hours. The mixture was then cooled momentarily in ice, 1.5 mL of methanol was added, and stirring was continued for 15 minutes at room temperature. This mixture was concentrated under reduced pressure, and the residual oil taken up in 15 mL of ethyl acetate; 5 mL of water was added and adjusted to pH 3 with N HCl. The organic phase was washed with water, dried ($Na_2SO_4$), decolorized with charcoal, and concentrated under reduced pressure. The residue was triturated with three 2 mL portions of ether, and the ether decanted. The residue was dissolved in 3 mL of ethyl acetate, and hexane was added to slight turbidity. On standing, a small amount of impurity separated which was removed by filtration. The solvent was evaporated under reduced pressure to leave 140 mg of product: NMR (Me$_2$SO-d$_6$) δ3.49 (s, 2H, PhCh$_2$), 3.55–3.90 (m, 2H, CHCH$_2$), 3.75 (d, J=12 Hz, 6H, MeOP), 4.90 (m, 1H, CHCH$_2$), 7.27 (s, 5H, Ph), 8.11 (s, 1H, CONHP), 8.75 (d, J=8 Hz, 1H, NHCH); IR (CHCl$_3$) 3440, 3320, 1790, 1727, 1680, 1050 cm$^{-1}$; mass spectrum m/z 356 (M+H)$^+$.

EXAMPLE II

Synthesis of (S)-N-[1-[[(Dimethoxyphosphinyl)amino]carboxyl]-2-oxo-3-azetidinyl]benzeneacetamide sodium salt 140 mg of product obtained in the previous Example was stirred with 7 mL of ethyl acetate and 8 mL of water, and adjusted to pH 7.5 by addition of N/10 NaOH. The aqueous phase was separated and freeze dried to yield 60 mg of product as a glassy solid: NMR (Me$_2$SO-d$_6$)δ3.27 (dd, J$_{4\alpha,4\beta}$=6 Hz and J$_{3,4\beta}$=3 Hz, 1H, CHCH$_\alpha$H$_{62}$), 3.45 (d, J=11 Hz, 6H, MeOP), 3.46 (s, 2H, PhCH$_2$), 3.67 (t, J$_{4\alpha,4\beta}$=J$_{3,4\alpha}$=6 Hz, 1H, CHCHαHβ), 4.72 (m, 1H, CHCH$_2$), 7.27 (s, 5H, Ph), 8.75 (d, J=8 Hz, 1H, NHCH); IR (KBr) 3280, 1768, 1677–1660, 1607, 1045 cm$^{-1}$.

EXAMPLE III

The activity of the compound produced in Example II, measured against a variety of organisms and expressed as the minimum inhibitory concentration, was determined using the microdilution broth method. The results of this test are given in Table I.

TABLE I

| Minimum Inhibitory Concentration (μg/mL) | |
| --- | --- |
| E. coli 257 | 32 |
| E. coli 48 | 32 |
| K. pneumoniae A | 64 |
| E. cloacae 9570A | 64 |
| P. vulgaris ATCC 6380 | 16 |
| P. vulgaris 503-1136 | 16 |
| P. mirabilis 190 | 16 |
| S. marcescens SM | 32 |
| P. aeruginosa Stone 130 | >128 |
| P. aeruginosa 503-56 | >128 |
| S. Pyoenes 503-782 | >128 |
| S. aureus Smith | 16 |

EXAMPLE IV

Alternative synthesis of (S)-N-[1-[[(Dimethoxyphosphinyl)amino]carbonyl]-2-oxo-3-azetidinyl]benzeneacetamide A mixture of 2.20 g (0.01 mol) of (S)-(2-oxo-3-azetidinyl)carbamic acid phenylmethyl ester, 40 mL of dry acetonitrile, 6.4 mL (4.85 g, 0.048 mol) of triethylamine and 1.6 mL (0.012 mol, based on 85% purity) of phosphorisocyanatidic acid dimethyl ester was warmed to 35° C. to obtain complete solution, and stirred at room temperature for 2 hours. An additional 0.8 mL of phosphorisocyanatidic acid dimethyl ester was then added and the mixture stirred for an additional 2 hours. With momentary cooling in ice, 15 mL of methanol was added, and stirring was continued for 15 minutes at room temperature. The mixture was concentrated to dryness under reduced pressure; CH$_2$Cl$_2$ was added to the residue, and the evaporation was repeated. The residual oil was taken up in CHCl$_3$. Water was added and adjusted to pH 3 with N HCl. The organic phase was dried (Na$_2$SO$_4$) and evaporated under reduced pressure. A solution of the residue in ethyl acetate was treated with charcoal, filtered, and concentrated to dryness under reduced pressure to leave 3.10 g of (S)-1-[[(Dimethoxyphosphinyl)amino]carbonyl-2-oxo-3-azetidinyl]carbamic acid phenylmethyl ester, as an oil.

A mixture of 185 mg (0.5 mmol) of the (S)-[1-[[(dimethoxyphosphinyl)amino]carbonyl]-2-oxo-3-azetidinyl]carbamic acid phenylmethyl ester thus produced, 185 mg of 10% Pd on carbon catalyst, and 8 mL of DMF was hydrogenated on a Parr apparatus at an initial gauge pressure of 50 psi. After five minutes, when hydrogenolysis was complete, the mixture was cooled in ice, under a nitrogen atmosphere, and 0.07 mL (0.5 mmol) of triethylamine and 0.07 mL (0.5 mmol) of phenylacetyl chloride were added. After stirring at 0°–5° C. for 3 hours, and addition of charcoal, the mixture was filtered through a bed of diatomaceous earth (Celite). The solvent was evaporated under reduced pressure, the residue taken up in ethyl acetate and water, and the pH adjusted to 3 with hydrochloric acid. The organic phase was washed with water, dried (Na$_2$SO$_4$), decolorized with charcoal, and concentrated under reduced pressure. The residual oil was triturated three times with ether (3 mL portions), and the ether decanted. The residue was then dissolved in CH$_2$Cl$_2$ and concentrated under reduced pressure to leave 20 mg of product.

EXAMPLE V

Alternative Synthesis of (S)-N-[1-[[(Dimethoxyphosphinyl)amino]carbonyl]-2-oxo-3-azetidinyl]benzeneacetamide A mixture of 105.6 mg (0.518 mmol) of (S)-N-(2-oxo-3-azetidinyl)benzeneacetamide, produced as in Example I, 6 mL of dimethoxyethane, and 2 mL of CH$_2$Cl$_2$ was stirred and cooled to 6° C.; 0.084 mL (0.776 mmol) of phosphorisocyanatidic dichloride was added, and stirring continued at 6°. After 15 minutes complete solution resulted. After an additional 45 minutes at 6° C., the mixture was cooled to −15°, and a solution of 0.216 mL of triethylamine, 0.125 mL of pyridine, and 1.5 mL of methanol was added. The resulting solution was stirred 1.5 hours at room temperature, and then concentrated under reduced pressure. A solution of the residue in CH$_2$Cl$_2$ was washed sequentially with water, 1N HCl, and brine, dried (MgSO$_4$), treated with charcoal, filtered, and concentrated to dryness under reduced pressure. The residue was triturated with two 4 mL portions of ether, the ether decanted, and residual solvent removed from the remaining oil under reduced pressure to leave 72 mg of product.

EXAMPLE VI

Synthesis of (S)-N-[1-[[(Dimethoxyphosphinyl)amino]carbonyl]-2-oxo-3-azetidinyl]acetamide A mixture of 925 mg (2.5 mmol) of (S)-[1-[[(dimethoxyphosphinyl)amino]-carbonyl]-2-oxo-3-azetidinyl]carbamic acid phenylmethyl ester, prepared as in Example IV, 40 mL of DMF, 300 mg of 10% palladium on charcoal catalyst, and 6.0 mL (30 mmol) of acetic anhydride was hydrogenated (5 minutes) on a Parr apparatus at an initial gauge pressure of 50 psi. After filtration of the catalyst, the mixture was concentrated to dryness under reduced pressure. The residual oil was triturated with petroleum ether (bp 30°–60° C.), and with ether, decanting each time. The residue was dissolved in methylene chloride, and the solution filtered with diatomaceous earth (Hyflo) after addition of charcoal. Evaporation of the solvent under reduced pressure gave 700 mg of product as an oil. NMR (Me$_2$SO-d$_6$) δ 1.87 (s,3H,MeCO), 3.59 (m, 1H, CHCH$_\alpha$CH$_\beta$), 3.72 (d, J=12 H$_z$, 6H, MeOP), 3.82 (t, J$_{4\alpha,4\beta}$=J$_{3,4\alpha}$=6.5 Hz, 1H, CHCH$_\alpha$H$_\beta$), 4.84 (m, 1H, CHCH$_2$), 8.15 (bs, 1H, NHP) 8.58 (d, J=8 Hz, 1H, NHCH); IR (CHCl$_3$) 3300, 1787, 1727, 1674, 1053 cm$^{-1}$; mass spectrum (FAB) m/z 280 (M+H)$^+$.

EXAMPLE VII

Synthesis of
[3S-(3β),(R*)]-α-[4-Ethyl-2,3-dioxo-1-piperazino-carbonyl)amino]-N-[1-[[(dimethoxyphosphinyl)amino]carbonyl]-2-oxo-3-azetidinyl]benzeneacetamide The reaction of [3S-(3β),(R*)]-α-[(4-Ethyl-2,3-dioxo-1-piperazinocarbonyl)amino]-2-oxo-3-azetidinyl]benzeneacetamide (0.21 g, 0.542 mmol) and phosphorisocyanatidic acid dimethylester (0.26 mL, 2.17 mmol) afforded the title compound (0.192 g, 65.8%) by a procedure similar to that used to prepare (S,Z)-2-[(chloroacetyl)amino]-α-methoxyimino-N-[1-[[dimethoxyphosphinyl)amino]carbonyl]-2-oxo-3-azetidinyl]-thiazole-4-acetamide, as described in Example VIII herein.

IR $_{max}^{KBr}$cm$^{-1}$: 3298, 1785, 1720, 1680, 1465, 1040.
NMR (DMSO-d$_6$): 1.13 (3H, t, J=7 Hz, Me), 3.76 (6H, d, J=11 Hz, Me), 3.30–4.05 (8H, m, C$_4$—H, CH$_2$, CH$_2$CH$_2$), 4.95 (1H, m C$_4$—H), 5.45 (1H, d, J=7 Hz, CH$_2$), 7.37 (5H, s, aromatic-H), 8.00 (1H, br.s, NH), 9.09 (1H, d, J=8 Hz, NH), 9.78 (1H, d, J=7 Hz, NH).

EXAMPLE VIII

Synthesis of
(S,Z)-2-Amino-α-(methoxyimino)-N-[1-[[dimethoxyphosphinyl)amino]carbonyl]-2-oxo-3-azetidinyl]-thiazole-4-acetamide Sodium Salt (a) A mixture of (S,Z)-[(chloroacetyl)amino]-α-methoxyimino-N-oxo-3-acetidinyl)thiazole-4-acetamide (0.656 g, 1.89 mmol) (obtainable by the method described in Reference Example 17/3 of European Patent Application No. 21,678, published July 1, 1981) and phosphorisocyanatidic acid dimethyl ester (0.9 mL, 7.59 mmol) in DMF (30 mL) was stirred at 55°–60° C. for 22 hr under argon. After removal of the solvent, the residue was treated with MeOH (10 mL) and the mixture was stirred at room temperature for 30 min. Evaporation of the solvent in vacuo gave the residue which was redissolved in CH$_2$Cl$_2$ (30 mL) and washed with water (30 mL) and brine (30 mL), and dried over anhyd.MgSO$_4$. The solvent was removed and the residue was treated with Et$_2$O to obtain (S,Z)-2-[(chloroacetyl)amino]-α-methoxyimino-N-[1-[[(dimethoxyphosphininyl)amino]carbonyl]-2-oxo-3-azetidinyl]thiazole-4-acetamide, as a powder.

(b) Sodium N-methyldithiocarbamate (0.068 g, 0.52 mmol) was added to a solution of the thus produced (S,Z)-2-[(chloroacetyl)amino]-α-methoxyimino-N-[1-[[(dimethoxyphosphinyl)amino]carbonyl]-2-oxo-3-azetidinyl]thiazole-4-acetamide (0.2 g, 0.4 mmol) in MeOH (6 mL)-H$_2$O(2 mL), and the resulting solution was stirred at room temperature for 70 min. After removal of the solvent, the residue was treated with AcOEt (5 mL) and extracted with water (5 mL, 2 times). The aqueous phase was then applied to an XAD-2 column which was eluted with 10%-EtOH to obtain the title compound.

IR $_{max}^{KBr}$cm$^{-1}$: 3315, 3200, 1780 (shoulder), 1770, 1670, 1632, 1535, 1335, 1040.
NMR (DMSO-d$_6$): 3.69 (6H, d, j=11 Hz, Me), 3.85 (3H, s, Me), 3.44–3.90 (2H, m, C$_4$—H), 4.90 (1H, m, C$_3$—H), 6.72 (1H, s, thiazole-H), 7.14 (2H, s, NH$_2$), 9.12 (1H, d, J=8 Hz, NH).

EXAMPLE IX

In a manner analogous to that described in Example I, intermediates of the formula

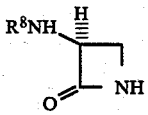

wherein R$^8$ is as specified in Table II below, are reacted with phosphorisocyanatidic acid dimethyl ester to yield compounds of the formula

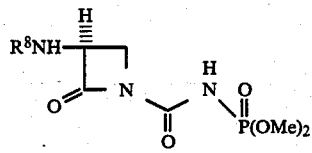

The specified intermediates are prepared by the methods described in the respective Examples of European Patent Application No. 21,678 indicated in Table II.

TABLE II

| R$^8$ | Example in European Patent Application No. 21,678 Giving Synthesis of Intermediate |
|---|---|
| NCCH$_2$CO— | Reference Example 17/8 |
| ⟨S⟩—CH$_2$CO— | Reference Example 17/2 |
| EtN(piperazinedione)NCNHCHCO—⟨S⟩ | Reference Example 17/42 |

TABLE II-continued

| $R^8$ | Example in European Patent Application No. 21,678 Giving Synthesis of Intermediate |
|---|---|
| [structure: n-C₈H₁₇N-piperazinedione-NCNHCH(C₆H₅)CO— (D)] | Reference Example 17/25 |
| [structure: CH₃C(O)NH-thiazole-CH=C(CHCO—)-NH-C(=O)-N-piperazine-2,3-dione-N-Et] | Reference Example 17/23 |
| [structure: ClCH₂CH₂N-piperazinedione-NCNHCH(C₆H₅)CO—] | Reference Example 17/102 |
| [structure: ClCH₂C(O)NH-thiazole-CH=C(CHCO—)-NH-C(=O)-N-piperazine-2,3-dione-N-n-C₈H₁₇] | Reference Example 17/27 |
| [structure: furan-CH=N-N(piperazinone)-NCNHCH(thiophene)CO—] | Reference Example 17/32 |
| [structure: nC₈H₁₇N-piperazinedione-NCNHCH(thiophene)CO—] | Reference Example 17/29 |
| [structure: EtN-piperazinedione-NCNHCH₂CH₂CHCO— with NH-C(=O)-N-piperazine-2,3-dione-N-Et] | Reference Example 17/100 |

TABLE II-continued

| $R^8$ | Example in European Patent Application No. 21,678 Giving Synthesis of Intermediate |
|---|---|
| EtN-[piperazine-2,3-dione]-N-C(O)NHCH(4-MeO-C6H4)CO— (D) | Reference Example 17/19 |
| ClCH2C(O)NH-[thiazol-2-yl]-C(=CHCH)-CH(NH-C(=O)-N-[1-ethyl-2,3-dioxopiperazinyl])-CO— | Reference Example 17/22 |
| 4-Cl-C6H4-C(O)NHC(O)NHCH(2-thienyl)CO— | Reference Example 17/48 |
| C6H5CH2OC(O)NHCH(C6H5)CO— (D) | Reference Example 17/6 |
| [3-(2,6-dichlorophenyl)-5-methylisoxazol-4-yl]CO— | Reference Example 17/10 |
| [1,2,3-triazol-1-yl]-CH2CO— | Reference Example 17/9 |
| C6H5CH(SO2NMe2)CO— | Reference Example 17/99 |
| C6H5CH2OC(O)NHCH(CH3)CO— (D) | Reference Example 17/12 |
| Et-N-[piperazine-2,3-dione]-N-C(O)NHCH(CH3)CO— (D) | Reference Example 17/17 |
| ClCH2C(O)NH-[thiazol-2-yl]-C(=CHCH)-CH2CO— | Reference Example 17/4 |

TABLE II-continued

| R[8] | Example in European Patent Application No. 21,678 Giving Synthesis of Intermediate |
|---|---|
|  | Reference Example 17/18 |

EXAMPLE X

Synthesis of [S-(Z)]-2-[[[1-(2-amino-4-thiazolyl)-1-[[1-[[(dimethoxyphosphinyl)amino]carbonyl]azetidinyl]amino]-2-oxoethylidene]imino]oxy]-2-methylpropanoic acid In a manner analogous to that described in Example 4 of European Patent Application No. 62,876, the protected acid (Z)-alpha-[[2-(1,1-Dimethylethoxy)-1,1-dimethyl-2-oxoethoxy]imino]-2-[(triphenylmethyl)amino]-4-thiazoleacetic acid is reacted with (S)-3-amino-2-azetidinone. The intermediate thus obtained is then further reacted with phosphorisocyanatidic acid dimethyl ester and triethylamine, in a manner analogous to that described in Example I hereof. Subsequent treatment with acid to remove the protecting groups yields the titled product.

EXAMPLE XI

Synthesis of [S-(Z)]-[[1-(2-Amino-4-thiazolyl)-2-[[1-[[(dimethoxyphosphinyl)amino]carbonyl-2-oxo-3-azetidinyl]amino]-2-oxoethylidene]imino]oxy]acetic acid In a manner analogous to that described in Example 4 of European Patent Application No. 62,876 the protected acid (Z)-alpha-[[[[2-(1,1-Dimethylethoxy)-2-oxoethoxy]imino]-2-triphenylmethyl]amino]-4-thiazoleacetic acid is reacted with (S)-3-amino-2-azetidinone. The intermediate thus obtained is then further reacted with phosphorisocyanatidic acid dimethyl ester and triethyl amine, in a manner analogous to Example I hereof. Subsequent treatment with acid to remove the protecting groups yields the titled product.

EXAMPLE XII

Synthesis of (3S-trans)-N-[1-[[(Dimethoxyphosphinyl)amino]carbonyl]-4-methyl-2-oxo-3-azetidinyl]benzeneacetamide By a procedure analogous to that of Example I, but starting with (3S-trans)methyl-azetidinyl)carbamic acid phenylmethyl ester the preparation of which is described in example 103 E, page 142 of South Africa Patent Application 810,808), the title compound was prepared: NMR (CDCl$_3$) δ1.53 (d,J=6 Hz, 3H, CH$_3$CH), 3.58 (s, 2H, C$_6$H$_5$CH$_2$), 3.83 (d, J=12.5 Hz, 6H, MeOP), 4.18 (m, 1H, CHMe), 4.40 (dd, J$_{H3,NH}$=7 Hz, J$_{H3,H4}$=3 Hz, 1H, CHNH), 7.16 (d, J=7 Hz, 1H, CHNH), 7.28 (s, 5H, C$_6$H$_5$), 7.63 (bs, 1H, NHP); IR (CHCl$_3$) 3430, 3300, 1783, 1727, 1680, 1043 cm$^{-1}$; mass spectrum m/z 369 (M+).

EXAMPLE XIII (a) Compounds analogous to those prepared as described in Example IX, having the formula,

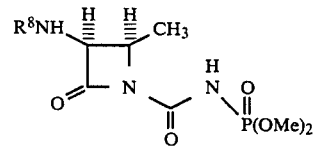

are prepared in a manner analogous to that described in Example IX, starting with intermediates of the formula

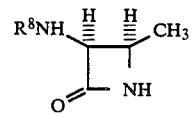

where R[8] is as specified in Table II of that Example.

(b) Compounds analogous to those prepared as described in Example IX, having the formula

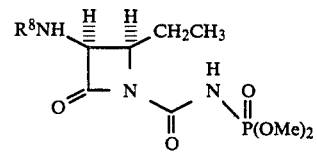

are prepared in a manner analogous to that described in Example IX, starting with intermediates of the formula

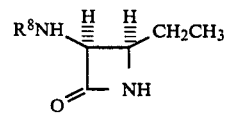

where R[8] is as specified in Table II of that Example.

EXAMPLE XIV (a) Synthesis of cis-rac-1[[(Dimethoxyphosphinyl)amino]carbonyl]-4-oxo-3-(phenylacetylamino)azetidine-2-carboxylic acid ethyl ester In a manner analogous to that described in Example I, but starting with rac-cis-3-(benzyloxycarboxycarbonylamino)-4-oxoazetidine-2-carboxylic acid ethyl ester, the title compound was prepared:
NMR (Me$_2$SO-d$_6$)δ1.04 (t,J=7 Hz,3H, MeCH$_2$), 3.49 (s, 2H, PhCH$_2$), 3.76 (d, J=12 Hz, 6H, MeOP), 3.96 (m, 2H, MeCH$_2$), 4.92 (d, J=6.5 Hz, 1H, CHCOOEt), 5.42 (dd, J$_{3,NH}$=8 Hz, J$_{2,3}$=6.5 Hz, NHCH), 7.24 (s,5H, Ph), 8.50 (bs, 1H, NHP), 9.07 (d,J=8 Hz, 1H, NHCH); IR (KBr) 3380-3300, 1800, 1737, 1680, 1033 cm$^{-1}$.

(b) Synthesis of cis-rac-1[[(Dimethoxyphosphinyl)amino]carbonyl]-4-oxo-3-(phenylacetylamino)azetidine-2-carboxylic acid methyl ester In a manner analogous to that described in Example I, but starting with rac-cis(benzyloxycarbonylamino)-4-oxoazetidine-2-carboxylic acid methyl ester, the title compound is prepared.

EXAMPLE XV

Compounds analogous to those prepared in Example IX, having the formula

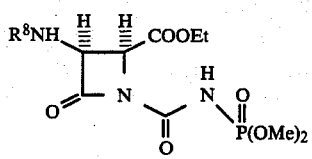

are prepared in a manner analogous to that described in Example IX, starting with intermediates of the formula

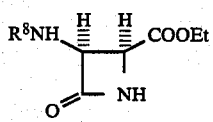

where $R^8$ is as specified in Table II of that Example.

EXAMPLE XVI

Synthesis of (S)-[1-[[[(bis-(Dimethylamino)phosphinyl]amino]carbonyl]-2-oxo-3-azetidinyl]carbamic acid phenylmethyl ester A mixture of 220 mg (1 mmol) of (S)-(2-oxo-3-azetidinyl)carbamic acid phenylmethyl ester, 6 mL of THF, and 6 mL of CH$_2$Cl$_2$ was stirred at 0° C. and 0.14 mL (1.4 mmol) of phosphorisocyanatidic acid dichloride was added. The reaction was maintained at 0° C. for one hour, and then further cooled to −50° C. A solution of 90 mg (2 mmol) of dimethylamine, 0.26 mL (3 mmol) of dry pyridine and 0.42 mL (3 mmol) of triethylamine in 2 mL of CH$_2$Cl$_2$ was added, and stirring was continued for two hours at −50° C. to −30° C. and for 30 minutes at −30° C. to −10° C. The mixture was then concentrated under reduced pressure and the residue dissolved in ice-water and EtOAc. The mixture was adjusted to pH 2 with H$_3$PO$_4$, the organic phase separated, and the aqueous phase again extracted with EtOAc. The organic extracts were combined, washed with brine, dried (Na$_2$SO$_4$), and concentrated under reduced pressure. The residue was redissolved in CH$_2$Cl$_2$, and again the solvent was evaporated under reduced pressure to yield 130 mg of the title compound: NMR (CDCl$_3$) δ2.73 (d, J=10.5 Hz, 12H, NMe), 3.80 (dd, J$_{4\alpha,4\beta}$=6 Hz and J$_{3,4\beta}$=3.5 Hz, 1H, CHCH$_{60}$H$_\beta$), 3.98 (t, J$_{3,4}$=J$_{4,4}$=6 Hz, 1H, CHCH$\alpha$H$\beta$), 4.84 (m, 1H, CHCH$_2$), 5.11 (s, 2H, CH$_2$O), 6.32 (d, J=7 Hz, 1H, NHCH), 7.32 (s, 5H, Ph); IR (CHCl$_3$) 3450, 3310, 1785, 1723 cm$^{-1}$.

EXAMPLE XVII

Synthesis of (S)-N-[1-[[[bis-(Dimethylamino)phoshinyl]amino]carbonyl]-2-oxo-3-azetidinyl]benzeneacetamide By a procedure analogous to that used in the second part of Example IV, (S)-[1-[[[bis-(dimethylamino)phophinyl]amino]carbonyl]2-oxo-3-azetidinyl]carbamic acid phenylmethyl ester, produced as in the previous Example, is hydrogenated in the presence of 10% Pd on carbon catalyst, and the intermediate thus obtained is acylated by reaction with phenylacetyl chloride and triethylamine to obtain the title compound.

EXAMPLE XVIII

Synthesis of (S)-N-[[[bis(dimethylamino)phosphinyl]amino]carbonyl]-2-oxo-3-azetidinyl]acetamide By a procedure analogous to that used in Example VI, a mixture of (S)-[1-[[[bis-(dimethylamino)-phosphinyl]amino]carbonyl]-2-oxo-3-azetidinyl]carbamic acid phenylmethyl ester, 10% Pd on carbon catalyst, DMF, and excess acetic anhydride is hydrogenated, to yield, after work up, the title compound.

EXAMPLE XIX

Manufacture of dry vials or ampoules for intramuscular administration 500 mg of a sterile lypholyzate of (S)-N-[1-[[(Dimethoxyphosphinyl)amino]carbonyl]-2-oxo-3-azetidinyl]-benzeneacetamide sodium salt is prepared, for instance as in Example I herein, and filled into a vial or ampoule. Before administration, 5 ml of water for injection is added in order to reconstitute the drug.

EXAMPLE XX

Manufacture of dry drug suitable for intravenous infusion 2 grams of a sterile lypholyzate of (S)-N-[1-[[(Dimethoxyphosphinyl)amino]carboxyl]-2-oxo-3-azetidinyl]-benzeneacetamide sodium salt is prepared and filled into a standard 50 ml intravenous infusion container. Prior to administration, the drug is reconstituted with 40 ml 0.9% sodium chloride solution for injection or 5% dextrose solution for injection.

EXAMPLE XXI

Manufacture of Soft Gelatin Capsule for Oral Administration

A soft gelatin capsule is filled with a composition consisting of the following:

| | |
|---|---|
| (S) N—[1[[(Dimethoxyphosphinyl)amino]carboxyl]-2-oxo-3-azetidinyl]benzeneacetamide sodium salt | 250 mg. |
| Mono-di- and tri-glycerides of fatty acids | 400 mg. |
| Lecithin | 100 mg. |
| | 750 mg. |

We claim:

1. A compound of the formula

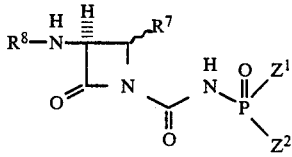

wherein, $Z^1$ is a group —$OR^1$, —$NR^3R^4$, or —$SR^5$, $Z^2$ is a group —$OR^2$, —$NR^3R^4$, or —$SR^6$;

$R^1$ and $R^2$ may be either the same or different and each is hydrogen, lower alkyl, aryl, thienyl, furyl, pyrrolyl, pyrazinyl, thiazolyl, pyrimidinyl or tetrazolyl;

$R^3$ and $R^4$ may be either the same or different and each is hydrogen, lower alkyl, aralkyl, aryl, thienyl, furyl, pyrrolyl, pyrazinyl, thiazolyl, pyrimidinyl or tetrazolyl;

$R^5$ and $R^6$ may be either the same or different and each is hydrogen, lower alkyl, aralkyl, aryl, thienyl, furyl, pyrrolyl, pyrazinyl, thiazolyl, pyrimidinyl or tetrazolyl;

$R^7$ is hydrogen, lower alkyl, or lower alkoxycarbonyl;

$R^8$ is acyl; and pharmaceutically acceptable salts thereof.

2. Compounds according to claim 1 wherein $Z^1$ and $Z^2$ are lower alkoxy or mono- or di-lower alkyamino.

3. Compounds according to claim 2 wherein $Z^1$ and $Z^2$ are lower alkoxy.

4. Compounds according to claim 3 wherein $Z^1$ and $Z^2$ are methoxy.

5. Compounds according to claim 2 wherein $Z^1$ and $Z^2$ are di-lower alkylamino.

6. Compounds according to claim 5 wherein $Z^1$ and $Z^2$ are dimethylamino.

7. Compounds according to claim 2 wherein $R^7$ is H.

8. Compounds according to claim 2 wherein $R^7$ is lower alkyl.

9. Compounds according to claim 8 wherein $R^7$ is methyl.

10. Compounds according to claim 2 wherein $R^7$ is lower alkoxycarbonyl.

11. Compounds according to claim 10 wherein $R^7$ is ethoxycarbonyl.

12. Compounds according to claim 3 wherein $R^7$ is H.

13. Compounds according to claim 3 wherein $R^7$ is lower alkyl.

14. Compounds according to claim 13 wherein $R^7$ is methyl.

15. Compounds according to claim 3 wherein $R^7$ is lower alkoxycarbonyl.

16. Compounds according to claim 15 wherein $R^7$ is ethoxycarbonyl.

17. Compounds according to claim 5 wherein $R^7$ is H.

18. Compounds according to claim 2 wherein $R^8$ is phenylacetyl or acetyl.

19. Compounds according to claim 3 wherein $R^8$ is phenylacetyl or acetyl.

20. Compounds according to claim 5 wherein $R^8$ is acetyl.

21. In accordance with claim 1, the compound (S)-N-[1-[[(Dimethoxyphosphinyl)amino]carbonyl]-2-oxo-3-azetidinylbenzeneacetamide, and pharmaceutically acceptable salts thereof.

22. In accordance with claim 1, the compound (S)-N-[1-[[(Dimethoxyphosphinyl)amino]carbonyl]-2-oxo-3-azetidinyl]-acetamide, and pharmaceutically acceptable salts thereof.

23. In accordance with claim 1, the compound [3S-(3β),(R*)]-α-[4-Ethyl-2,3-dioxo-1-piperazino-carbonyl)amino]-N-[1-[[(dimethoxyphosphinyl)amino]-2-oxo-3-azetidinyl]benzeneacetamide, and pharmaceutically acceptable salts thereof.

24. In accordance with claim 1, the compound (S,Z)-2-Amino-α-(methoxyimino)-N-[1-[[dimethoxyphosphinyl)amino]carbonyl]-2-oxo-3-azetidinyl]thiazole-4-acetamide, and pharmaceutically acceptable salts thereof.

25. In accordance with claim 1, the compound (35-trans)-N-[1-[[(Dimethoxyphosphinyl)amino]carbonyl-4-methyl-2-oxo-3-azetidinyl]benzeneacetamide, and pharmaceutically acceptable salts thereof.

26. In accordance with claim 1, the compound cis-rac-1-[[(Dimethoxyphosphinyl)amino]-carbonyl]-4-oxo-3-(phenylacetylamino)azetidine-2-carboxylic acid ethyl ester, and pharmaceutically acceptable salts thereof.

27. In accordance with claim 1, the compound (S)-[1-[[[bis(Dimethylamino)phosphinyl]amino]carbonyl]-2-oxo-3-azetidinyl]carbamic acid phenylmethyl ester, and pharmaceutically acceptable salts thereof.

* * * * *